United States Patent
Augeri et al.

(10) Patent No.: US 10,604,480 B2
(45) Date of Patent: Mar. 31, 2020

(54) (THIO, OXO, AND SELENO) SEMICARBAZONE DERIVATIVES AND THEIR USE FOR TREATING CANCER

(71) Applicants: RUTGERS, THE STATE UNIVERSITY OF NEW JERSEY, New Brunswick, NJ (US); THE RESEARCH FOUNDATION FOR THE STATE UNIVERSITY OF NEW YORK, Syracuse, NY (US)

(72) Inventors: David J. Augeri, New Brunswick, NJ (US); Anthony F. Bencivenga, New Brunswick, NJ (US); Adam Blanden, Syracuse, NY (US); Darren R. Carpizo, New Brunswick, NJ (US); John A. Gilleran, New Brunswick, NJ (US); Spencer David Kimball, New Brunswick, NJ (US); Stewart N. Loh, Syracuse, NY (US); Xin Yu, New Brunswick, NJ (US)

(73) Assignees: Rutgers, The State University of New Jersey, New Brunswick, NJ (US); The Research Foundation for the State University of New York, Syracuse, NY (US)

( * ) Notice: Subject to any disclaimer, the term of this patent is extended or adjusted under 35 U.S.C. 154(b) by 0 days.

(21) Appl. No.: 15/545,968

(22) PCT Filed: Jan. 27, 2016

(86) PCT No.: PCT/US2016/015177
§ 371 (c)(1),
(2) Date: Jul. 24, 2017

(87) PCT Pub. No.: WO2016/123242
PCT Pub. Date: Aug. 4, 2016

(65) Prior Publication Data
US 2018/0002280 A1 Jan. 4, 2018

Related U.S. Application Data

(60) Provisional application No. 62/108,415, filed on Jan. 27, 2015, provisional application No. 62/258,236, filed on Nov. 20, 2015.

(51) Int. Cl.
| | |
|---|---|
| C07D 337/08 | (2006.01) |
| C07C 337/08 | (2006.01) |
| C07D 403/12 | (2006.01) |
| C07D 401/14 | (2006.01) |
| C07D 401/12 | (2006.01) |
| C07D 205/04 | (2006.01) |
| C07D 213/68 | (2006.01) |
| A61K 31/175 | (2006.01) |
| A61K 31/397 | (2006.01) |

(Continued)

(52) U.S. Cl.
CPC .......... *C07C 337/08* (2013.01); *A61K 31/175* (2013.01); *A61K 31/397* (2013.01); *C07C 281/08* (2013.01); *C07D 205/04* (2013.01); *C07D 213/53* (2013.01); *C07D 213/68* (2013.01); *C07D 401/12* (2013.01); *C07D 401/14* (2013.01); *C07D 403/12* (2013.01)

(58) Field of Classification Search
CPC .. C07D 337/08; C07D 281/08; A61K 31/175; A61K 31/397
See application file for complete search history.

(56) References Cited

U.S. PATENT DOCUMENTS 4,665,173 A * 5/1987 Klayman ............ C07D 213/53
540/583
2013/0345164 A1 12/2013 Vazquez et al.
(Continued)

FOREIGN PATENT DOCUMENTS

WO 2001094340 A1 12/2001
WO 2006019955 A2 2/2006
(Continued)

OTHER PUBLICATIONS

Yu, Cancer Cell, vol. 21, 616-625, 2012. (Year: 2012).*
(Continued)

*Primary Examiner* — D Margaret M Seaman
(74) *Attorney, Agent, or Firm* — Vilksnins Harris Padys Malen LLP

(57) ABSTRACT

The invention provides compounds of formula I and II and salts thereof, wherein $R^1$, $R^2$, Y, $R^3$, and $R^4$ have any of the meanings described in the specification, as well as compositions comprising such compounds and salts, and methods for treating cancer using such compounds and salts.

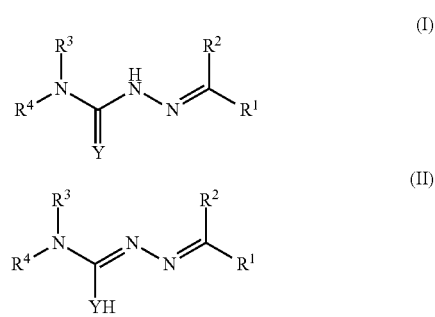

28 Claims, No Drawings

(51) Int. Cl.
C07C 281/08 (2006.01)
C07D 213/53 (2006.01)

(56) References Cited

U.S. PATENT DOCUMENTS

| | | | |
|---|---|---|---|
| 2014/0142266 | A1 | 5/2014 | Sakamoto et al. |
| 2018/0000772 | A1 | 1/2018 | Augeri et al. |
| 2018/0000806 | A1 | 1/2018 | Augeri et al. |
| 2018/0002279 | A1 | 1/2018 | Augeri et al. |

FOREIGN PATENT DOCUMENTS

| | | | |
|---|---|---|---|
| WO | 2006101740 | A2 | 9/2006 |
| WO | 2007035489 | A2 | 3/2007 |
| WO | 2009039553 | A1 | 4/2009 |
| WO | 2012/175962 | * | 12/2012 |
| WO | 2015021456 | A1 | 2/2015 |
| WO | 2016123246 | A1 | 8/2016 |
| WO | 2016123250 | A1 | 8/2016 |
| WO | 2016123253 | A1 | 8/2016 |

OTHER PUBLICATIONS

Agrawal, J Med Chem, 1976, vol. 19(7), 970-972. (Year: 1975).*
Antonini, J Med Chem, 1977, vol. 20(3), 447-449. (Year: 1977).*
Huang, J Med Chem, 2010, vol. 53(8), 3048-3064. (Year: 2010).*
Mrozek-Wilczkiewicz, ACS Med Chem Letters, 2014, vol. 5(4), 336-339. (Year: 2014).*
Kalinowski, J Med Chem, 2007, vol. 50(15), 3716-3729. (Year: 2007).*
Kodela, J Pharm Exp Ther 345:85-94, Apr. 2013. (Year: 2013).*
Chhabra, Int J appl Basic Med Res, Jan.-Jun. 2013, 3(1), 16-18. (Year: 2013).*
SIngh, IJPSR, 2014, vol. 5(11), 4644-4659. (Year: 2014).*
Patani, Chem Rev, 1996, vol. 96, 3147-3176. (Year: 1996).*
U.S. Appl. No. 15/545,966, 2018-0002279.
U.S. Appl. No. 15/545,971, 2018-0000806.
U.S. Appl. No. 15/545,975, 2018-0000772.
Bellitto, et al., "Conformational Studies of Some Potentially Bidentate Thiosemicarba-zones and Related Complexes of Zinc(II)", J.C.S. Dalton 68570(21), 758-762 (1976).
Chun-Ying, et al., "Synthesis, Crystal Structure and Nonlinear Optical Properties of Thiosemicarbazone Zinc Complex", J Coord Chem 47, 433-439 (1999).
Easmon, et al., "2-benzoxazolyl and 2-benzimidazolyl hydrazones derived from 2-acetylpyridine: a novel class of antitumor agents", Int J Cancer 94, 89-96 (2001).
Easmon, et al., "Synthesis, Structure—Activity Relationships, and Antitumor Studies of 2-Benzoxazolyl Hydrazones Derived from Alpha-(N)-acyl Heteroaromatics", J Med Chem 49, 6343-6350 (2006).
Easmon, et al., "Thiazolyl and benzothiazolyl hydrazones derived from α-(N)-acetylpyridines and diazines: synthesis, antiproliferative activity and CoMFA studies", Eur J Med Chem 32, 397-408 (1997).
File CAPLUS, "Preparation and characterization of vanillin thiosemicarbazone complexes with cobalt(II), nickel(II), copper(II), zinc(II), cadmium(II), and mercury(II)", STN CA Caesar Accession No. 1170, 2 pages. (1984).
File CAPLUS, "Synthesis and crystal structure of zinc(II) complex [Zn(25-MBTSC)212]", STN CA Caesar Accession No. 1162, 1 page (2013).
File CAPLUS, "Synthesis and structure of 1.5Zn(phen)3.cntdot.L. cntdot..3N03 supramolecule (phen = o-phenanthroline, L = 4-aminoacetophenone thiosemicarbazone", STN CA Caesar Accession No. 1176, 2 pages (2008).
Hall, et al., "Investigations on the Mechanism of Action of the Novel Antitumor Agents 2-Benzothiazolyl, 2-Benzoxazolyl, and 2-Benzimidazolyl Hydrazones Derived from 2-Acetylpyridine", Arch Pharm Pharm Med Chem 332 (4), 115-123 (1999).
Huang, et al., "Correlating gene expression with chemical scaffolds of cytotoxic agents: ellipticines as substrates and inhibitors of MDR1", Pharmacogenomics Journal 5, 112-125 (2005).
Ibrahim, et al., "Indole-7-carbaldehyde thiosemicarbazone as a flexidentate ligand toward ZnII, CdII, PdII and PtII ions: cytotoxic and apoptosis-inducing properties of the PtII complex", Dalton Trans 43, 3860-3860 (2014).
Khalaji, et al., "Synthesis and Characterization of Zinc(II) Complexes with 3,4-Dimethoxybenzaldehyde Thiosemicarbazone: The Crystal Structure of [Zn(34-MBTSC) 2 Cl 2 ]", Phosphorus, Sulfur, and Silicon 188, 1119-1126 (2013).
Kovala-Demertzi, et al., "Zinc(II) complexes derived from pyridine-2-carbaldehyde thiosemicarbazone and (1E)-1-pyridin-2-ylethan-1-one thiosemicarbazone. Synthesis, crystal structures and antiproliferative activity of zinc(II) complexes", Journal of Inorganic Biochemistry 100, 1558-1567 (2006).
Mohan, et al., "Synthesis, Characterization, and Antitumor Properties of some Metal Complexes of 2,6-Diacetylpyridine Bis(N4-azacyclic Thiosemicarbazone)", Journal of Inorganic Biochemistry 34, 41-54 (1988).
Moorthy, et al., "QSAR analysis of 2-benzoxazolyl hydrazone derivatives for anticancer activity and its possible target prediction", Med Chem Res 21, 133-144 (2012).
Patent Cooperation Treaty, International Searching Authority, Search Report and Written Opinion for PCT/US2016/015177, 15 pages, dated Mar. 24, 2016.
Priyadharsini, et al., "Docking, synthesis, characterization and evaluation of novel cdk2 inhibitors: benzothiazole derivatives", International Journal of Pharmacy and Pharmaceutical Sciences 4(3), 574-585 (2012).
Ren, et al., "A new approach to suppress nonlinearity-transparency trade-off through coordination chemistry: syntheses and spectroscopic study on second-order nonlinear optical properties of a series of square-pyramidal zinc (II) complexes", Spectrochimica Acta Part A 59, 1095-1101 (2003).
Richardson, et al., "Dipyridyl Thiosemicarbazone Chelators with Potent and Selective Antitumor Activity Form Iron Complexes with Redox Activity", J Med Chem 49, 6510-6521 (2006).
Ruangpornvisuti, et al., "A DFT investigation of conformational geometries and interconversion equilibria of phenylthiosemicarbazone and its complexation with zinc", J Mol Model 10, 418-426 (2004).
Sleebs, et al., "Discovery of Potent and Selective Benzothiazole Hydrazone Inhibitors of Bcl-XL", J Med Chem 56, 5514-5540 (2013).
Tian, et al., "Structural characterization and second-order nonlinear optical properties of zinc halide thiosemicarbazone complexes", Polyhedron 21, 1217-1222 (2002).
Todorovic, et al., "Synthesis and characterization of Zn(II) and Cd(II) complexes with 2,6-diacetylpyridine-bis (selenosemicarbazone). Crystal structure of a Ni(II) complex with a modified 2,6-diacetylpyridine-bis (selenosemicarbazone)", Inorganic Chemistry Communications 9, 862-865 (2006).
Webster, et al., "Synthesis and characterization of novel pentagonal bipyramidal compleses of iron(II), cobalt(II), and zinc(II)", Journal of American Chemical Society 95(19), 6505-6506 (1973).
Yu, et al., "Small molecule restoration of wildtype structure and function of mutant p53 using a novel zinc-metallochaperone based mechanism", Oncotarget 5(19), 8879-8892 (2014).
Gudasi, et al., "Synthesis and spectral investigation of some transition metal complexes containing pentadentate macroacyclic NNNNN-donor Schiff base ligands", Transition Metal Chemistry 30, 726-732 (2005).
Bermejo, E , et al., "Complexes of Grup 12 Metals with 2-Acetylpyridine 4N-Dimethyl-thiosemiearbazone and with 2-Acetyipyridine-N-oxide 4N-Dimethyl-thiosemiearbazone: Synthesis, Structure and Antifungal Activity", Zeitschrift fuer Naturforschung, B: Chemical Sciences 54(6), 777-787 (1999).
Bjelogrlic, S , et al., "Synthesis, structure and characterization of novel Cd(II) and Zn(II) complexes with the condensation product of 2-formylpyridine and selenosemicarbazide Antiproliferative activity of the synthesized complexes and related selenosemicarbazone complexes", Journal of Inorganic Biochemistry 104, 673-682 (2010).

(56) References Cited

OTHER PUBLICATIONS

Khaled, S , et al., "Synthesis and Spectroscopic Characterization of Some NOvel Polypyridine and Phenanthroline Complexes of Mn(II), Fe(II), Co(II) and Zn(II) Incorporating a Bidentate Benzothiazolyl Hydrazone Ligand", Chem Sci Trans 2(4), 1222-1231 (2013).
Odashima, T , et al., "Determination of Microamounts of Iron by Extraction-Spectrophotometry with 2-Acetylpyridine-2-benzothiazolylhydrazone and Its Sensitization by Employing an Analog Derivative Technique", Microchemical Journal 33, 138-146 (1986).

\* cited by examiner

(THIO, OXO, AND SELENO) SEMICARBAZONE DERIVATIVES AND THEIR USE FOR TREATING CANCER

CROSS-REFERENCE TO RELATED APPLICATIONS

This patent application claims the benefit of priority of U.S. application Ser. No. 62/108,415, filed Jan. 27, 2015, and of U.S. application Ser. No. 62/258,236, filed Nov. 20, 2015, which applications are herein incorporated by reference.

BACKGROUND OF THE INVENTION

TP53 is the most commonly mutated gene in human cancer for which no effective targeted anti-cancer drug exists. The majority of TP53 mutations (>70%) are missense mutations that generate a defective protein that is generally found at high levels in cancer cells due to loss of MDM2 negative feedback. Restoring the function of p53 in mouse models of cancer is highly therapeutic. Reactivating mutant p53 using small molecules has been highly sought after, yet remains an elusive goal in the development of cancer therapeutics.

SUMMARY OF THE INVENTION

The invention provides novel compounds, compositions, and methods for treating cancer. More specifically, one aspect of the present invention provides a compound of formula (I) or (II):

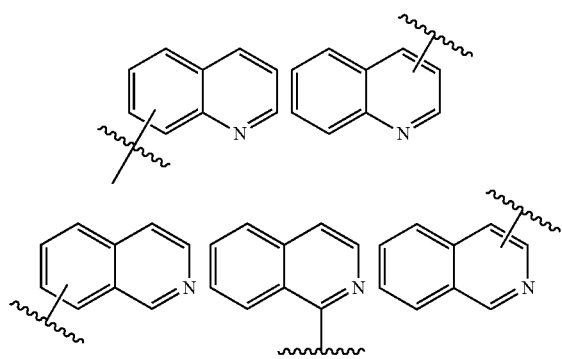

wherein:

$R^1$ is selected from the group consisting of:

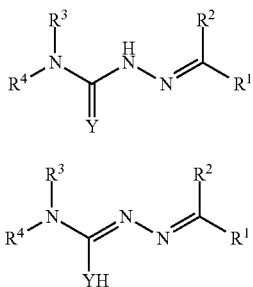

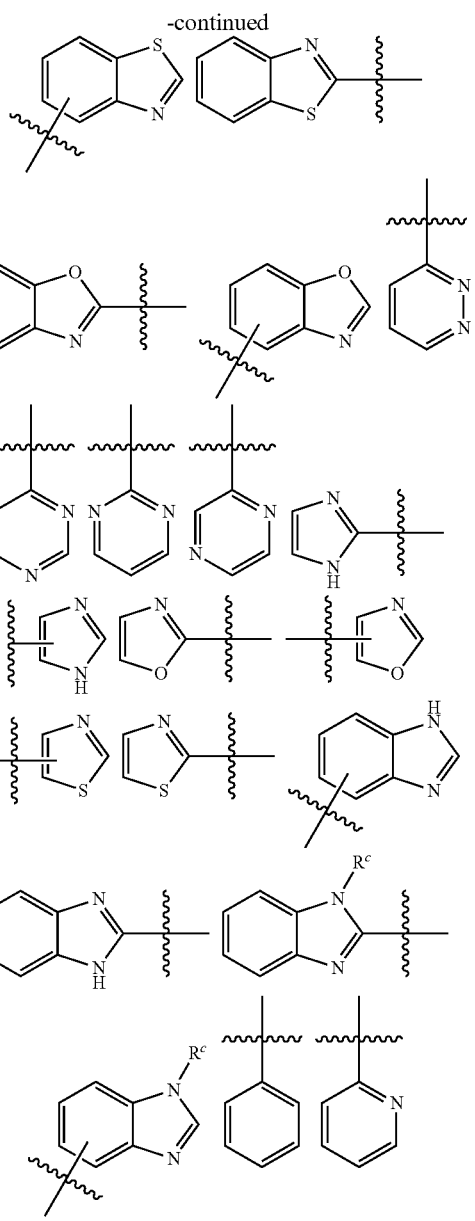

wherein $R^1$ is optionally substituted with one or more groups independently selected from halo, cyano, hydroxy, nitro, $—N(R^a)_2$, carboxy, phenyl, $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkanoyl, $(C_1-C_6)$alkoxycarbonyl, $(C_2-C_6)$alkanoyloxy, $(C_4-C_6)$heterocycloalkyl, $(C_2-C_6)$alkylaminocarbonyl and $(C_2-C_6)$alkanoylamino wherein any phenyl, $(C_1-C_6)$alkyl, $(C_2-C_6)$alkenyl, $(C_2-C_6)$alkynyl, $(C_1-C_6)$alkoxy, and $(C_3-C_6)$cycloalkyl, is optionally substituted with one or more groups independently selected from halo, cyano, hydroxy, nitro, $—N(R^a)_2$, carboxy, $(C_3-C_6)$cycloalkyl, $(C_1-C_6)$alkoxy, $(C_1-C_6)$alkanoyl, $(C_1-C_6)$alkoxycarbonyl, $(C_2-C_6)$alkanoyloxy, $(C_4-C_6)$heterocycloalkyl, $(C_2-C_6)$alkylaminocarbonyl and $(C_2-C_6)$alkanoylamino;

$R^2$ is selected from the group consisting of H, phenyl, heteroaryl, $(C_1-C_6)$alkyl, $(C_2-C_6)$alkenyl, $(C_2-C_6)$alkynyl, and $(C_3-C_6)$cycloalkyl, wherein any phenyl, heteroaryl, $(C_1-C_6)$alkyl, $(C_2-C_6)$alkenyl, $(C_2-C_6)$alkynyl, and $(C_3-C_6)$cycloalkyl is optionally substituted with one or more groups independently selected from halo, —N($R^b$)$_2$, ($C_3$-$C_6$)cycloalkyl, ($C_1$-$C_6$)alkoxy, ($C_2$-$C_6$)alkanoyloxy, ($C_2$-$C_6$) alkoxycarbonyl, ($C_2$-$C_6$) alkylaminocarbonyl, and ($C_2$-$C_6$) alkanoylamino;

Y is S, O, Se;

$R^3$ and $R^4$ are each independently selected from H, ($C_1$-$C_6$)alkyl, piperidinyl, or piperazinyl, which piperidinyl or piperazinyl is optionally substituted with pyridyl; or $R^3$ and each $R^4$ taken together with the nitrogen to which they are attached form a 3, 4, 5, 6, 7, 8, or 9 membered ring that is optionally substituted with one or more groups independently selected from the group consisting of halo;

each $R^a$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$) alkynyl, ($C_3$-$C_6$)cycloalkyl, ($C_1$-$C_6$)alkanoyl, and ($C_1$-$C_6$) alkoxycarbonyl, is optionally substituted with one or more groups independently selected from halo, ($C_3$-$C_6$)cycloalkyl, and ($C_1$-$C_6$)alkoxy; or two $R^a$ taken together with the nitrogen to which they are attached form a azetidino, pyrrolidino, piperidino, or morpholino ring;

each $R^b$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$) alkynyl, ($C_3$-$C_6$)cycloalkyl, ($C_1$-$C_6$)alkanoyl, and ($C_1$-$C_6$) alkoxycarbonyl, is optionally substituted with one or more groups independently selected from halo, ($C_3$-$C_6$)cycloalkyl, and ($C_1$-$C_6$)alkoxy; or two $R^b$ taken together with the nitrogen to which they are attached form a azetidino, pyrrolidino, piperidino, or morpholino ring; and each $R^c$ is independently selected from the group consisting of H and ($C_1$-$C_6$)alkyl that is optionally substituted with one or more groups independently selected from halo, ($C_3$-$C_6$)cycloalkyl, and ($C_1$-$C_6$)alkoxy;

or a salt thereof;

provided that if $R^1$ is 2-pyridinyl, then $R^2$ is not H or ($C_1$-$C_6$)alkyl.

Another aspect of the present invention provides a pharmaceutical composition, comprising, a compound of formula I or a pharmaceutically acceptable salt thereof, and a pharmaceutically acceptable carrier.

Another aspect of the present invention provides a method of inhibiting cancer cell growth, comprising contacting the cancer cell with an effective amount of a compound of formula I or a salt thereof.

Another aspect of the present invention provides a method of treating cancer in an animal (e.g. a human), comprising administering to the animal a compound of formula I or a pharmaceutically acceptable salt thereof.

The invention further includes methods of preparing, methods of separating, and methods of purifying the compounds described herein.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

DESCRIPTION OF THE INVENTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term allyl as used herein refers to a substituent, molecular fragment, or radical having the chemical formula —$CH_2$—CH—$CH_2$.

The term "butyl" as used herein refers to a four-carbon alkyl radical, substituent, or molecular fragment having the chemical formula —$C_4H_9$.

The term "cyclopropyl" as used herein refers to a radical, substituent, or molecular fragment having a chemical structure derived from cyclopropane and having the chemical formula $C_3H_5$.

The term "ethyl" as used herein refers to an alkyl substituent, radical, or molecular fragment having the chemical formula —$C_2H_5$.

The term "isopropyl" as used herein refers to a propyl with a group attached to the secondary carbon.

The term "methyl" as used herein refers to an alkyl derived from methane and containing one carbon atom bonded to three hydrogen atoms and having the chemical formula —$CH_3$.

The term "propyl" as used herein refers to a linear three-carbon alkyl substituent, molecular fragment, or radical having the chemical formula —$C_3H_7$.

The term "phenyl" refers to a cyclic group of atoms, radical, substituent, or molecular fragment having the chemical formula —$C_6H_5$.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; and $(C_2-C_6)$alkanoyloxy can be acetoxy, propanoyloxy, butanoyloxy, isobutanoyloxy, pentanoyloxy, or hexanoyloxy.

The ability of ZMC1, NTA ($Zn^{2+}$-binding homolog), and A6 (structural homolog) to increase intracellular $[Zn^{2+}]_{free}$ was evaluated by treating cells with the fluorescent $Zn^{2+}$ indicator FluoZin-3-AM (FZ3-AM) in complete media and imaging them using confocal microscopy. In both HEK293 (non-cancer, p53-WT) and TOV112D (ovarian cancer, p53-R175H) cells, ZMC1 increased intracellular $[Zn^{2+}]_{free}$ as indicated by increased fluorescence, but NTA and A6 did not. This result is consistent with the metallochaperone (MC) model for ZMC1 function and explains the inability of NTA and A6 to reactivate p53-R175H at micromolar concentrations. Of the two control compounds, A6 shuttled $Zn^{2+}$ into the liposomes, but NTA did not.

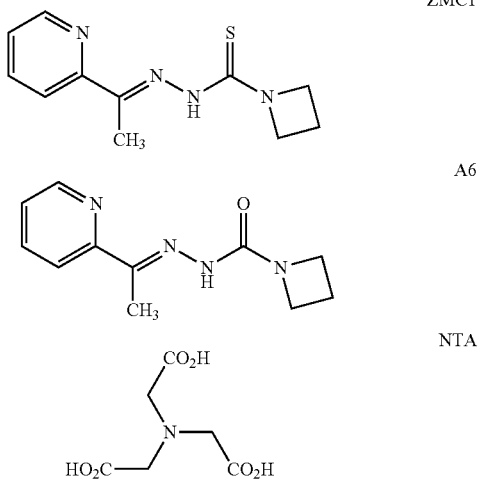

NTA binds $Zn^{2+}$ with an affinity similar to that of ZMC1, but it cannot cross either liposomal or cellular membranes, likely because it possesses negative charges. A6, on the other hand, lacks charges and is similar in structure to ZMC1, but binds $Zn^{2+}$ weakly ($K_d=1.1$ μM). It can function as an ionophore in conditions of the liposome experiments where external $[Zn^{2+}]_{free}$ was 10 μM. However, in complete media containing 10% fetal bovine serum (FBS), $Zn^{2+}$-binding proteins from the serum (e.g. albumin) necessarily compete for $Zn^{2+}$ with any putative MC, making the effective $[Zn^{2+}]_{free}$ much lower than $[Zn^{2+}]_{total}$. A6 therefore likely does not increase intracellular $[Zn^{2+}]_{free}$ in culture because $K_{d,A6}$ is greater than extracellular $[Zn^{2+}]_{free}$. Thus, both an appropriate $Zn^{2+}$ $K_d$ and ionophore activity influence ZMC1 activity. To determine whether ZMC1 can traverse lipid bilayers as a free compound, the $[Zn^{2+}]_{free}$ gradient was reversed by adding a large excess of metal ion chelator EDTA to the solution outside of the liposomes; fluorescence was monitored in the presence and absence of ZMC1. EDTA alone did not cause a significant decrease in RZ-3 fluorescence as the liposomal membranes are impermeable to EDTA. After subsequent addition of ZMC1, there was a time dependent decrease in RZ-3 fluorescence. This result indicates that free ZMC1 crossed the liposomal membranes, bound internal $Zn^{2+}$, and transported it back outside the liposome where the metal was then bound by the much stronger chelator EDTA. Thus, ZMC1 can cross biological membranes both as free drug and drug-$Zn^{2+}$ complex, and therefore can transport $Zn^{2+}$ into cells without becoming trapped as either species.

To ensure that the fluorescence results were due to $Zn^{2+}$ transport and not to non-specific disruption of liposomal membranes, a liposomal leakage assay was performed using the self-quenching fluorophore calcein. When calcein is encapsulated at concentrations above 4 mM its fluorescence is decreased via self-quenching. Leakage is detected by a fluorescence increase as the dye dilutes and its fluorescence dequenches. At the highest concentrations of ZMC1 and $ZnCl_2$ a significant fluorescence increase was not detected. Disruption of liposomes can also be detected by alteration of their size distribution. The size distribution of liposomes treated with the highest concentrations of $ZnCl_2$ and ZMC1 was identical to that of untreated liposomes. Together, these data indicate the liposomal membranes remained intact upon ZMC1 treatment, and therefore the RZ-3 fluorescence changes are attributable only to specific $Zn^{2+}$ transport.

Characterization of ZMC1-Mediated $Zn^{2+}$ Transport in Live Cells

To extend the investigation of ZMC1 as an ionophore to living systems, ZMC1-mediated $Zn^{2+}$ transport was quantified in cells. The kinetics of intracellular $[Zn^{2+}]_{free}$ increase was measured by loading HEK293 and TOV112D cells with FZ3-AM, treating the cells with ZMC1 and $ZnCl_2$, and monitoring fluorescence by time-lapse microscopy. To minimize the potential for $Zn^{2+}$ contamination and contributions from poorly defined elements in complete media (e.g. FBS), cells were treated and imaged in $Ca^{2+}$ and $Mg^{2+}$-free Earle's Balanced Salt Solution supplemented with 10 mM HEPES pH 7.4 (EBSS/H (−)Ca/Mg). Excess $ZnCl_2$ with the $Zn^{2+}$ ionophore pyrithione (PYR) was used as a positive control. Excess membrane-permeable $Zn^{2+}$ chelator N,N,N',N'-tetrakis(2-pyridylmethyl)ethane-1,2-diamine (TPEN) was used as a negative control. When treated with $ZnCl_2$ alone or ZMC1 alone, neither cell type showed an increase in intracellular $[Zn^{2+}]_{free}$. When treated with both ZMC1 and $ZnCl_2$, both cell lines showed a time dependent increase at two different $ZnCl_2$ concentrations, demonstrating that both ZMC1 and extracellular $Zn^{2+}$ are required. When the fluorescence increases were fit to first-order exponentials, both concentrations of $ZnCl_2$ yielded identical half-lives in their respective cell types, which we combine to report $t_{1/2}$ (HEK293)=124±20 s and $t_{1/2}$ (TOV112D)=156±50 s (mean±SD, n=4).

The steady-state intracellular $[Zn^{2+}]_{free}$ of both cell types was then quantified after treatment with the 2:1 ratio of ZMC1:$ZnCl_2$. Cells were again loaded with FZ3-AM, treated with 1 μM ZMC1 and 0.5 μM $ZnCl_2$ in EBSS/H (−)Ca/Mg, and imaged as above. To normalize for differential dye loading, cells were then sequentially treated with excess PYR/$ZnCl_2$, imaged, treated with TPEN, and imaged again. PYR/ZnCl$_2$ and TPEN served to saturate and apoize the intracellular FZ3, respectively. In the absence of drug an intracellular $[Zn^{2+}]_{free}$ of 0.69±0.25 nM was measured for HEK293 cells and 0.71±0.19 nM was measured for TOV112D cells. These values reflect the lower limit of detection by FZ3-AM and are likely overestimates. Upon treatment with ZMC1 and ZnCl$_2$ intracellular $[Zn^{2+}]_{free}$ rose to 18.1±4.7 nM for HEK293 cells and 15.8±2.5 nM for TOV112D cells. These concentrations are theoretically sufficient to reactivate ~90% of p53-R175H based on the $K_{d1}$ value of 2.1 nM measured for DBD-R175H.

Materials and Methods
Reagents

FZ3-AM, RZ-3 (K$^+$ salt), and cell culture media were purchased from Life Technologies. DOPC was purchased from Avanti Polar Lipids. ZMC1 and A6 were similarly obtained. $Zn^{2+}(ZMC1)_2$ was synthesized and crystallized. HEK293 and TOV112D cells were purchased from ATCC and maintained in DMEM+GlutaMAX with 10% FBS and 1 mg/mL penicillin-streptomycin under a 5% CO$_2$ atmosphere at 37° C. All non-cell based experiments were conducted in 50 mM Tris pH 7.2, 0.1 M NaCl at 25° C.

Liposome Import Assay

DOPC-liposomes were prepared by film rehydration and extrusion followed by gel filtration and diluted to an OD$_{600}$=0.06 in buffer. The size distribution of the liposomes was determined by dynamic light scattering (DLS) using a Malvern Zetasizer Nano ZS. Fluorescence measurements were taken on a Horiba Fluoromax-4 spectrofluorimeter in a 5×5 mm quartz cuvette with $\lambda_{ex}/\lambda_{em}$=550/572 nm for RZ-3 and 490/515 nm for calcein. Initial Zn$^{2+}$ import/export was quantified by fitting the first 10-30 s of data after each treatment to a line and converted to units of flux using the following Eqn 1:

$$J_i = \frac{\Delta F}{\Delta t} \cdot \left(\frac{F_{max} - F_{min}}{[RZ3]}\right) \cdot \left(\frac{SA}{Vol}\right) \quad \text{Eqn 1}$$

where $J_i$ is the initial flux, $\Delta F/\Delta t$ is the slope of the fit line, $F_{max}$ is RZ-3 fluorescence in the presence of saturating Zn$^{2+}$ and 1% TritonX-100, $F_{min}$ is RZ-3 fluorescence in the presence of excess EDTA and 1% TritonX-100, [RZ3] is the concentration of encapsulated RZ-3, and SA/Vol is the surface area to volume ratio calculated assuming hollow spheres of the mean diameter determined by DLS.

Intracellular $[Zn^{2+}]_{free}$ Imaging

TOV112D or HEK293 cells (40,000 cells/well) were plated on either 8-well BD Falcon chambered culture slides (Corning Life Sciences) or 8-chambered #1.5 Nunc Lab-Tek II chambered coverglasses (Thermo Scientific) treated with poly-L-lysine. After 48 h, cells were washed 2×5 m in serum-free media and incubated with 1 µM FZ3-AM for 40 m at 37° C. Cells were then washed 2×5 m in either EBSS/H (−)Ca/Mg or phenol-red free DMEM+10% FBS containing the indicated treatments for 20 m before imaging. For nuclear colocalization, 1 µg/mL Hoechst 33342 was also included. Cells were imaged using a Zeiss LSM50 META NLO confocal microscope equipped with 37° C. environmental control chamber. FZ3 and Hoechst 33342 were excited at 488 nm (argon laser) and 790 nm (Chameleon Ti:sapphire laser), respectively. To determine the kinetics of fluorescence change, each background-subtracted image in the time-lapse series was integrated in ImageJ and normalized to the integrated fluorescence of the first frame after treatment. For quantification of intracellular $[Zn^{2+}]_{free}$, each cell was analyzed in the treated, 50 µM PYR/ZnCl$_2$ (1:1), and 100 µM TPEN images by taking the mean fluorescence of an ROI inside the cell subtracted by an ROI immediately outside the cell measured in ImageJ. The $[Zn^{2+}]_{free}$ for each cell was then calculated by Eqn 2:

$$[ZN^{2+}]_{free} = \frac{F - F_{min}}{F_{max} - F} \cdot K_d \quad \text{Eqn. 2}$$

Where F, $F_{max}$, and $F_{min}$ are fluorescence in the treatment, PYR/ZnCl$_2$, and TPEN images, respectively, and $K_d$ is that of FZ3 for Zn$^{2+}$ (15 nM) (31). To minimize the effects of outliers the lowest and highest 5% of cells in each series were rejected, and the remaining values averaged to give the value from that experiment. The number of cells analyzed in each trial ranged from 54-163. For nuclear colocalization, treated, PYR/ZnCl$_2$, and TPEN treated images costained with Hoechst 33342 were aligned and each pixel subjected to Eqn. 2 in MATLAB (MathWorks). The resultant images were Gaussian mean filtered and false-colored by calculated $[Zn^{2+}]_{free}$.

p53-R175H Immunofluorescence

DMEM+10% FBS was treated with 5 g Chelex 100 resin per 100 mL media for 1 hour with gentle shaking. The media was then decanted and filtered through 0.2 µm sterile filter. TOV112D cells were then incubated with 1 µM ZMC1 in untreated media, Chelex-treated media, or media+10 µM TPEN at 37° C. for 2 h, fixed, and stained with PAB240 and PAB1640.

Assays:

Cell growth inhibition assay using human tumor cell lines with different p53 status (wildtype, null, p53-R175H) were employed to determine if wildtype structure is restored to mutant p53 after treatment with a zinc metallochaperone.

An immunofluorescence assay using conformation specific antibodies was used to determine if a test compound could induce a wildtype conformation of mutant p53.

The invention will now be illustrated by the following non-limiting Examples.

EXAMPLES

Example 1

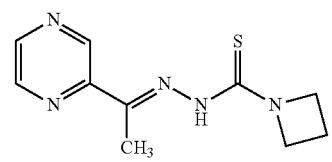 [SMILES: C/C(=N\NC(=S)N1CCC1)c1cnccn1]

(E)-N'(1-(Pyrazin-2-yl)ethylidene)azetidine-1-carbothiohydrazide (1) General Method A To a solution of azetidine-1-carbothiohydrazide (156 mg, 1.19 mmol, 1.0 eq) and 1-(pyrazin-2-yl)ethan-1-one (152 mg, 1.25 mmol, 1.05 eq) in DCM (6 ml) was added AcOH (4 drops). After stirring overnight at room temperature, the reaction was concentrated under reduced pressure and recrystallized from MeOH to afford 1 as a crystalline white solid (132 mg, 0.56 mmol, 47%). $^1$H-NMR (400 MHz, CDCl$_3$) δ 2.38 (t, J=7.72 Hz, 1H), 2.42 (t, J=7.88 Hz, 1H), 4.36 (br. t, J=7.52 Hz, 1H), 4.73 (br. t, J=7.40 Hz, 1H), 8.50 (d, J=2.56 Hz, 1H), 8.53 (m, 1H), 8.78 (s, 1H, NH), 9.13 (m, 1H). MS: 236.1 [M+H]⁺.

Example 2

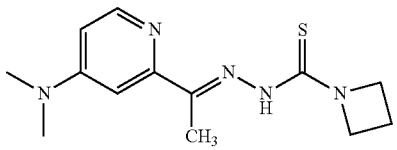 [SMILES: C/C(=N\NC(=S)N1CCC1)c1cc(N(C)C)ccn1]

(E)-N'-(1-(4-(dimethylamino)pyridin-2-yl)ethylidene)azetidine-1-carbothiohydrazide (2)

Following General Method A for the condensation of azetidine-1-carbothiohydrazide and 1-(4-(dimethylamino)pyridin-2-yl)ethan-1-one the title compound 2 was isolated as a white solid after recrystallization from MeOH. ¹H-NMR (400 MHz, CDCl₃) δ 2.34 (m, 5H), 3.02 (s, 6H), 4.34 (m, 2H), 4.70 (m, 2H), 6.49 and 6.54 (E/Z dd, J=6.04 Hz, 2.64 Hz, 1H), 6.62 and 7.08 (E/Z d, J=2.44 Hz, 1H), 8.26 (m, 1H), 8.71 (br. s, 1H, NH). MS: 278.0 [M+H]⁺.

Example 3

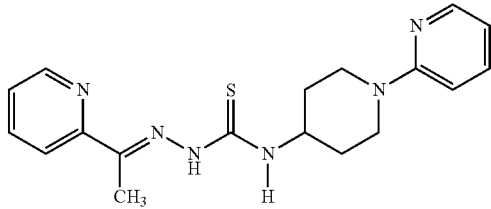 [SMILES: C/C(=N\NC(=S)NC1CCN(c2ccccn2)CC1)c1ccccn1]

(E)-2-(1-(pyridin-2-yl)ethylidene)-N-(1-(pyridin-2-yl)piperidin-4-yl)hydrazine-1-carbothioamide (3)

Following General Method A for the condensation of N-(1-(pyridin-2-yl)piperidin-4-yl)hydrazinecarbothioamide and 1-(pyridin-2-yl)ethan-1-one the title compound 3 was isolated as a white solid after recrystallization from MeOH. ¹H-NMR (400 MHz, CDCl₃) δ 1.76 (ddd, J=15.33 Hz, 11.72 Hz, 3.92 Hz, 2H), 2.30 (m, 2H), 2.42 (s, 3H), 3.04 (dt, J=13.73 Hz, 2.40 Hz, 2H), 3.72 (m, 2H), 4.57 (m, 1H), 7.16 and 7.19 (E/Z d, 1.56 Hz, 1H), 7.21 and 7.24 (E/Z m, 1H), 7.30 (ddd, J=5.87 Hz, 4.92 Hz, 1.04 Hz), 7.52 (br. d, J=8.16 Hz, 1H, NH), 7.72 (dt, J=7.76 Hz, 1.72 Hz, 1H), 7.90 (d, J=8.04 Hz, 1H), 8.11 (dd, J=4.44 Hz, 1.32 Hz, 1H), 8.35 (d, J=2.68 Hz, 1H), 8.61 (d, J=4.12 Hz, 1H), 8.68 (br. s, 1H, NH). MS: 287.0 [M+H]⁺.

Example 4

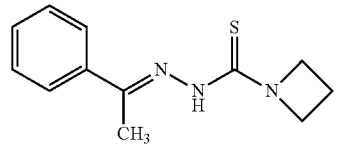 [SMILES: C/C(=N\NC(=S)N1CCC1)c1ccccc1]

(E)-N'-(1-phenylethylidene)azetidine-1-carbothiohydrazide (4)

Following General Method A for the condensation of azetidine-1-carbothiohydrazide and acetophenone, the title compound 4 was isolated as a white solid after recrystallization from MeOH. ¹H-NMR (400 MHz, CDCl₃) δ 2.33 (t, J=7.80 Hz, 1H), 2.37 (t, J=7.88 Hz, 1H), 4.33 (m, 2H), 4.69 (m, 2H), 7.37 (m, 3H), 7.65 (m, 2H), 8.63 (br. s, 1H, NH). MS: 234.1 [M+H]⁺.

Examples 5 and 6

The compounds of Examples 4 and 5 were prepared using General Method A. The structures, names, NMR data and mass spectral data for the compounds of Examples 5 and 6 are shown in Table 1.

TABLE 1

| Ex | Structure and Name | ¹H NMR MS |
|---|---|---|
| 5 | (E)-N'-(1-(6-hydroxylmethyl)pyridin-2-yl)ethylidene)azetidine-1-carbothiohydrazide | ¹H NMR (500 MHz, DMSO-d₆) δ 10.16 (s, 1H), 7.78 (dt, J = 15.7, 8.0 Hz, 2H), 7.43 (d, J = 6.9 Hz, 1H), 5.41 (t, J = 5.9 Hz, 1H), 4.56 (d, J = 5.8 Hz, 4H), 4.10 (s, 2H), 2.31 (s, 3H), 2.27-2.18 (m, 2H). (MS + H)+ 265 |

TABLE 1-continued

| Ex | Structure and Name | ¹H NMR MS |
|---|---|---|
| 6 | 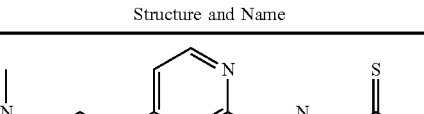<br>mixture of diastereomers<br><br>(E)-2-(1-(4-(2-(dimethylamino)ethoxy)-pyridin-2-yl)ethylidene)-N,N-dimethylhydrazine-1-carbothioamide | ¹H NMR (500 MHz, DMSO-$d_6$) δ 9.61 (bs, 1H), 8.43 (d, J = 5.7 Hz, 1H), 7.57 (s, 1H), 7.07-6.98 (m, 1H), 4.32-4.22 (m, 2H), 3.32 (s, 6H), 2.94 (bs, 2H), 2.62 (s, 3H), 2.42 (s, 6H). (MS + H)+ 310.05 |

Cell-based TOV112D activity for representative compounds is shown in Table 2.

TABLE 2

| Example | Structure | TOV112D IC$_{50}$* |
|---|---|---|
| 1 | 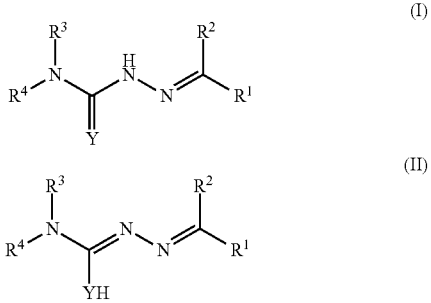 | ++ |
| 2 | 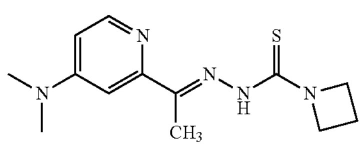 [SMILES: C/C(=N\NC(=S)N1CCC1)c1cc(N(C)C)ccn1] | +++ |
| 4 | 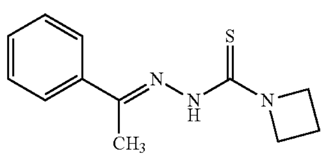 [SMILES: C/C(=N\NC(=S)N1CCC1)c1ccccc1] | + |
| 6 | mixture of diastereomers | + |

*+++, most active;
++, moderately active;
+, less active,
− no measureable activity All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound selected from compounds of formulas (I) and (II):

(I)

(II)

or a salt thereof, wherein:

$R^1$ is selected from the group consisting of:

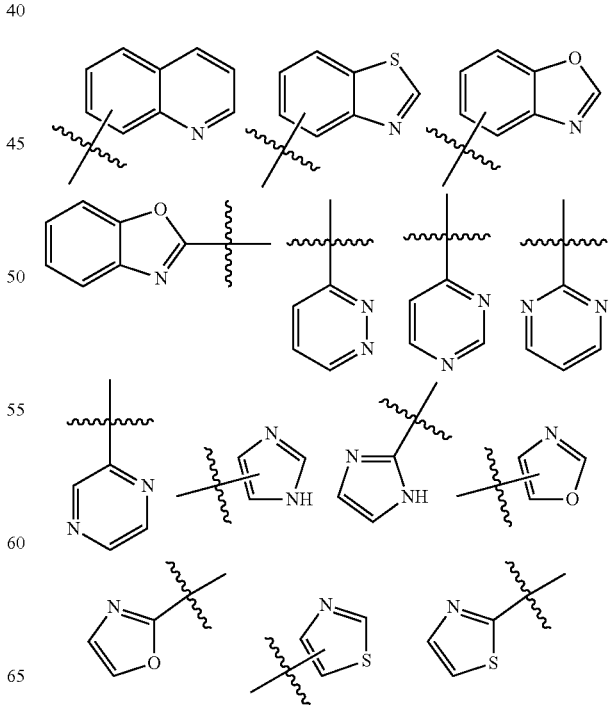

-continued

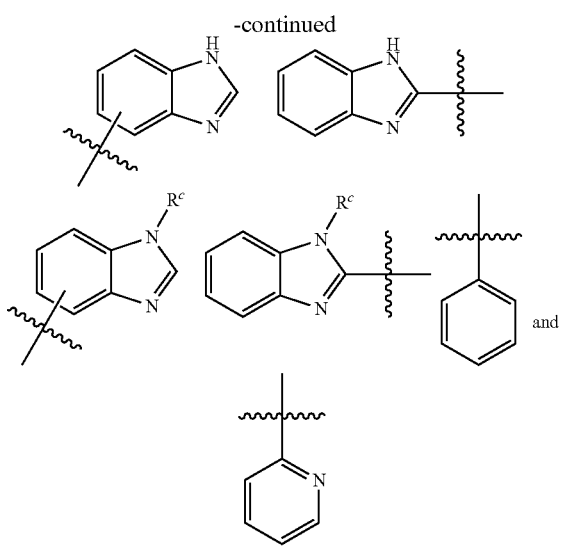

wherein R¹ is optionally substituted with one or more groups independently selected from halo, cyano, —N(R$^a$)$_2$, carboxy, phenyl, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkoxy, (C$_1$-C$_6$)alkanoyl, (C$_1$-C$_6$)alkoxycarbonyl, (C$_2$-C$_6$)alkanoyloxy, (C$_4$-C$_6$)heterocycloalkyl, (C$_2$-C$_6$)alkylaminocarbonyl and (C$_2$-C$_6$)alkanoylamino wherein any phenyl, (C$_1$-C$_6$)alkyl, (C$_2$-C$_6$)alkenyl, (C$_2$-C$_6$)alkynyl, (C$_1$-C$_6$)alkoxy, and (C$_3$-C$_6$)cycloalkyl, is optionally substituted with one or more groups independently selected from halo, cyano, hydroxy, nitro, —N(R$^a$)$_2$, carboxy, (C$_3$-C$_6$)cycloalkyl, (C$_1$-C$_6$)alkoxy, (C$_1$-C$_6$)alkanoyl, (C$_1$-C$_6$)alkoxycarbonyl, (C$_2$-C$_6$)alkanoyloxy, (C$_4$-C$_6$)heterocycloalkyl, (C$_2$-C$_6$)alkylaminocarbonyl and (C$_2$-C$_6$)alkanoylamino;

R² is selected from the group consisting of H, (C$_1$-C$_6$)alkyl, (C$_2$-C$_6$)alkenyl, (C$_2$-C$_6$)alkynyl, and (C$_3$-C$_6$)cycloalkyl, wherein any (C$_1$-C$_6$)alkyl, (C$_2$-C$_6$)alkenyl, (C$_2$-C$_6$)alkynyl, and (C$_3$-C$_6$)cycloalkyl is optionally substituted with one or more groups independently selected from halo, —N(R$^b$)$_2$, (C$_3$-C$_6$)cycloalkyl, (C$_1$-C$_6$)alkoxy, (C$_2$-C$_6$)alkanoyloxy, (C$_2$-C$_6$)alkoxycarbonyl, (C$_2$-C$_6$) alkylaminocarbonyl, and (C$_2$-C$_6$) alkanoylamino;

provided that if R¹ is 2-pyridinyl, then R² is not H or (C$_1$-C$_6$)alkyl;

Y is S, O, Se;

R³ is selected from H, (C$_1$-C$_6$)alkyl, piperidinyl, and piperazinyl, which piperidinyl or piperazinyl is optionally substituted with pyridyl;

R⁴ is selected from (C$_1$-C$_6$)alkyl, piperidinyl, and piperazinyl, which piperidinyl or piperazinyl is optionally substituted with pyridyl; or R³ and each R⁴ taken together with the nitrogen to which they are attached form a 3, 4, 5, 6, 7, or 8 membered ring that is optionally substituted with one or more groups independently selected from the group consisting of halo;

each R$^a$ is independently selected from the group consisting of H, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkanoyl, and (C$_1$-C$_6$)alkoxycarbonyl, wherein any (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkanoyl, and (C$_1$-C$_6$)alkoxycarbonyl, is optionally substituted with one or more groups independently selected from halo, (C$_3$-C$_6$)cycloalkyl, and (C$_1$-C$_6$) alkoxy; or two R$^a$ taken together with the nitrogen to which they are attached form a azetidino, pyrrolidino, piperidino, or morpholino ring;

each R$^b$ is independently selected from the group consisting of H, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkanoyl, and (C$_1$-C$_6$) alkoxycarbonyl, wherein any (C$_1$-C$_6$)alkyl, (C$_2$-C$_6$) alkenyl, (C$_2$-C$_6$)alkynyl, (C$_3$-C$_6$)cycloalkyl, (C$_1$-C$_6$) alkanoyl, and (C$_1$-C$_6$)alkoxycarbonyl, is optionally substituted with one or more groups independently selected from halo, (C$_3$-C$_6$)cycloalkyl, and (C$_1$-C$_6$) alkoxy; or two R$^b$ taken together with the nitrogen to which they are attached form a azetidino, pyrrolidino, piperidino, or morpholino ring; and each R$^c$ is independently selected from the group consisting of H and (C$_1$-C$_6$)alkyl that is optionally substituted with one or more groups independently selected from halo, (C$_3$-C$_6$)cycloalkyl, and (C$_1$-C$_6$)alkoxy.

2. A compound selected from the group consisting of:

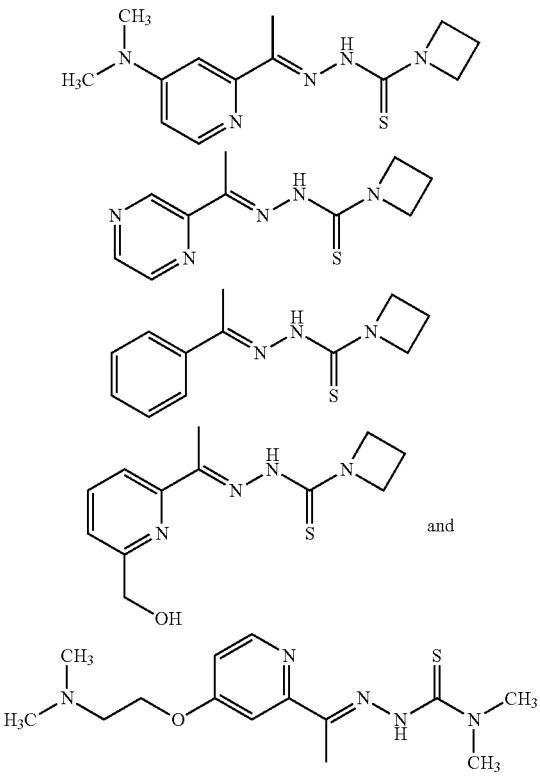

or a salt thereof.

3. A pharmaceutical composition, comprising, a compound of claim 1 or a pharmaceutically acceptable salt thereof, and a pharmaceutically acceptable carrier.

4. An injectable pharmaceutical formulation comprising, a compound of claim 1 or a pharmaceutically acceptable salt thereof, and a pharmaceutically acceptable carrier.

5. A method of inhibiting cancer cell growth in vivo or in vitro, comprising contacting a cancer cell with a compound of claim 1 or a pharmaceutically acceptable salt thereof.

6. A method of treating cancer in an animal comprising administering a compound of claim 1 or a pharmaceutically acceptable salt thereof to the animal.

7. The method of claim 6, further comprising administering zinc to the animal.

8. The method of claim 6, wherein the cancer is caused by mutations affecting zinc binding proteins.

9. The method of claim 6, wherein the cancer is associated with a zinc binding p53 mutation.

10. The method of claim 6, wherein the cancer is associated with a zinc binding p53 mutation selected from R175, C176, H179, C238, C242, and G245.

11. A pharmaceutical composition, comprising, a compound of claim 2 or a pharmaceutically acceptable salt thereof, and a pharmaceutically acceptable carrier.

12. An injectable pharmaceutical formulation comprising, a compound of claim 2 or a pharmaceutically acceptable salt thereof, and a pharmaceutically acceptable carrier.

13. A method of inhibiting cancer cell growth in vivo or in vitro, comprising contacting a cancer cell with a compound of claim 2 or a pharmaceutically acceptable salt thereof.

14. A method of treating cancer in an animal comprising administering a compound of claim 2 or a pharmaceutically acceptable salt thereof to the animal.

15. The method of claim 14, further comprising administering zinc to the animal.

16. The method of claim 14, wherein the cancer is caused by mutations affecting zinc binding proteins.

17. The method of claim 14, wherein the cancer is associated with a zinc binding p53 mutation.

18. The method of claim 14, wherein the cancer is associated with a zinc binding p53 mutation selected from R175, C176, H179, C238, C242, and G245.

19. A compound selected from compounds of formulas (I) and (II):

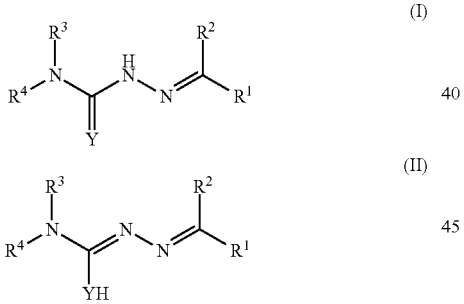

(I)

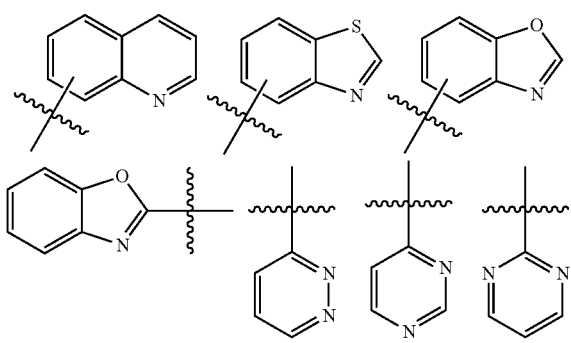

(II)

or a salt thereof, wherein:

$R^1$ is selected from the group consisting of:

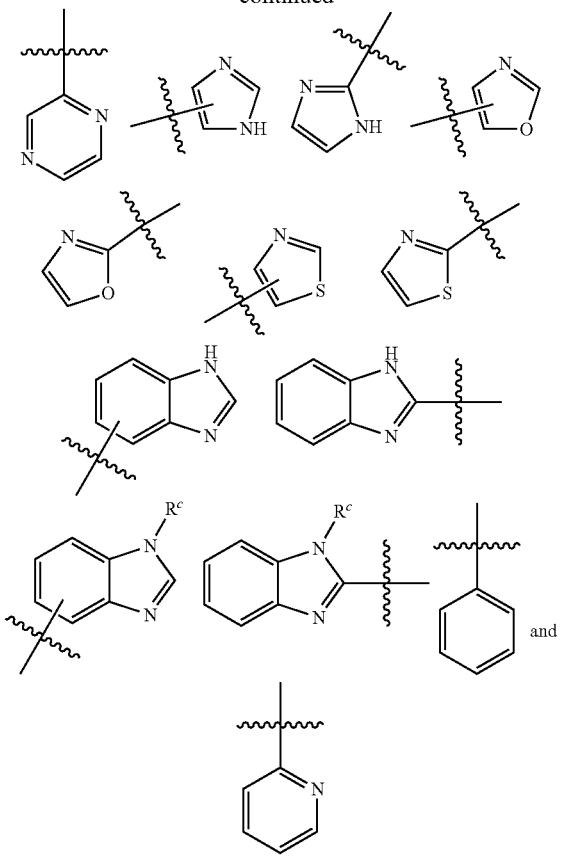

wherein $R^1$ is optionally substituted with one or more groups independently selected from halo, cyano, —N($R^a$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$) alkoxy, ($C_1$-$C_6$)alkanoyl, ($C_1$-$C_6$)alkoxycarbonyl, ($C_2$-$C_6$)alkanoyloxy, ($C_4$-$C_6$)heterocycloalkyl, ($C_2$-$C_6$) alkylaminocarbonyl and ($C_2$-$C_6$)alkanoylamino wherein any phenyl, ($C_1$-$C_6$)alkyl, ($C_2$-$C_6$)alkenyl, ($C_2$-$C_6$)alkynyl, ($C_1$-$C_6$)alkoxy, and ($C_3$-$C_6$)cycloalkyl, is optionally substituted with one or more groups independently selected from halo, cyano, hydroxy, nitro, —N($R^a$)$_2$, carboxy, ($C_3$-$C_6$)cycloalkyl, ($C_1$-$C_6$) alkoxy, ($C_1$-$C_6$)alkanoyl, ($C_1$-$C_6$)alkoxycarbonyl, ($C_2$-$C_6$)alkanoyloxy, ($C_4$-$C_6$)heterocycloalkyl, ($C_2$-$C_6$) alkylaminocarbonyl and ($C_2$-$C_6$)alkanoylamino;

$R^2$ is selected from the group consisting of H, ($C_1$-$C_6$) alkyl, ($C_2$-$C_6$)alkenyl, ($C_2$-$C_6$)alkynyl, and ($C_3$-$C_6$)cycloalkyl, wherein any ($C_1$-$C_6$)alkyl, ($C_2$-$C_6$)alkenyl, ($C_2$-$C_6$)alkynyl, and ($C_3$-$C_6$)cycloalkyl is optionally substituted with one or more groups independently selected from halo, —N($R^b$)$_2$, ($C_3$-$C_6$)cycloalkyl, ($C_1$-$C_6$)alkoxy, ($C_2$-$C_6$)alkanoyloxy, ($C_2$-$C_6$)alkoxycarbonyl, ($C_2$-$C_6$) alkylaminocarbonyl, and ($C_2$-$C_6$) alkanoylamino;

provided that if $R^1$ is 2-pyridinyl, then $R^2$ is not H or ($C_1$-$C_6$)alkyl;

Y is S, O, Se;

$R^3$ and $R^4$ are each independently selected from H, ($C_1$-$C_6$)alkyl, piperidinyl, or piperazinyl, which piperidinyl or piperazinyl is optionally substituted with pyridyl; or $R^3$ and each $R^4$ taken together with the nitrogen to which they are attached form a 3, 4, 5, 6, 7, or 8 membered ring that is optionally substituted with one or more groups independently selected from the group consisting of halo;

each $R^a$ is independently selected from the group consisting of $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two $R^a$ taken together with the nitrogen to which they are attached form a azetidino, pyrrolidino, piperidino, or morpholino ring;

each $R^b$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two $R^b$ taken together with the nitrogen to which they are attached form a azetidino, pyrrolidino, piperidino, or morpholino ring; and each $R^C$ is independently selected from the group consisting of H and $(C_1-C_6)$alkyl that is optionally substituted with one or more groups independently selected from halo, $(C_3-C_6)$cycloalkyl, and $(C_1-C_6)$alkoxy.

20. A compound selected from compounds of formulas (I) and (II):

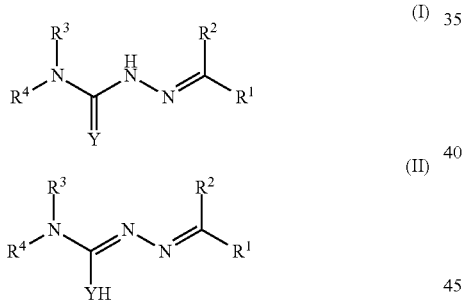

or a salt thereof, wherein:

$R^1$ is selected from the group consisting of:

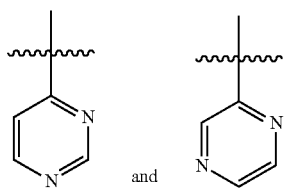 [SMILES: *c1ccncn1 ; *c1cnccn1]

and wherein $R^1$ is optionally substituted with one or more groups independently selected from halo, cyano, hydroxy, nitro, —$N(R^a)_2$, carboxy, phenyl, $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkanoyl, $(C_1-C_6)$alkoxycarbonyl, $(C_2-C_6)$alkanoyloxy, $(C_4-C_6)$heterocycloalkyl, $(C_2-C_6)$alkylaminocarbonyl and $(C_2-C_6)$alkanoylamino wherein any phenyl, $(C_1-C_6)$alkyl, $(C_2-C_6)$alkenyl, $(C_2-C_6)$alkynyl, $(C_1-C_6)$alkoxy, and $(C_3-C_6)$cycloalkyl, is optionally substituted with one or more groups independently selected from halo, cyano, hydroxy, nitro, —$N(R^a)_2$, carboxy, $(C_3-C_6)$cycloalkyl, $(C_1-C_6)$alkoxy, $(C_1-C_6)$alkanoyl, $(C_1-C_6)$alkoxycarbonyl, $(C_2-C_6)$alkanoyloxy, $(C_4-C_6)$heterocycloalkyl, $(C_2-C_6)$alkylaminocarbonyl and $(C_2-C_6)$alkanoylamino;

$R^2$ is selected from the group consisting of H, phenyl, heteroaryl, $(C_1-C_6)$alkyl, $(C_2-C_6)$alkenyl, $(C_2-C_6)$alkynyl, and $(C_3-C_6)$cycloalkyl, wherein any phenyl, heteroaryl, $(C_1-C_6)$alkyl, $(C_2-C_6)$alkenyl, $(C_2-C_6)$alkynyl, and $(C_3-C_6)$cycloalkyl is optionally substituted with one or more groups independently selected from halo, —$N(R^b)_2$, $(C_3-C_6)$cycloalkyl, $(C_1-C_6)$alkoxy, $(C_2-C_6)$alkanoyloxy, $(C_2-C_6)$alkoxycarbonyl, $(C_2-C_6)$alkylaminocarbonyl, and $(C_2-C_6)$ alkanoylamino;

Y is S, O, Se;

$R^3$ and $R^4$ are each independently is selected from H, $(C_1-C_6)$alkyl, piperidinyl, and piperazinyl, which piperidinyl or piperazinyl is optionally substituted with pyridyl; or $R^3$ and each $R^4$ taken together with the nitrogen to which they are attached form a 3, 4, 5, 6, 7, 8, or 9 membered ring that is optionally substituted with one or more groups independently selected from the group consisting of halo;

each $R^a$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two $R^b$ taken together with the nitrogen to which they are attached form a azetidino, pyrrolidino, piperidino, or morpholino ring;

each $R^b$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two $R^b$ taken together with the nitrogen to which they are attached form a azetidino, pyrrolidino, piperidino, or morpholino ring; and each $R^c$ is independently selected from the group consisting of H and $(C_1-C_6)$alkyl that is optionally substituted with one or more groups independently selected from halo, $(C_3-C_6)$cycloalkyl, and $(C_1-C_6)$alkoxy.

21. A pharmaceutical composition, comprising, a compound of claim 20 or a pharmaceutically acceptable salt thereof, and a pharmaceutically acceptable carrier.

22. An injectable pharmaceutical formulation comprising, a compound of claim 20 or a pharmaceutically acceptable salt thereof, and a pharmaceutically acceptable carrier.

23. A method of inhibiting cancer cell growth in vivo or in vitro, comprising contacting a cancer cell with a compound of claim 20 or a pharmaceutically acceptable salt thereof.

24. A method of treating cancer in an animal comprising administering a compound of claim 20 or a pharmaceutically acceptable salt thereof to the animal.

25. The method of claim 24, further comprising administering zinc to the animal.

26. The method of claim 24, wherein the cancer is caused by mutations affecting zinc binding proteins.

27. The method of claim 24, wherein the cancer is associated with a zinc binding p53 mutation.

28. The method of claim 24, wherein the cancer is associated with a zinc binding p53 mutation selected from R175, C176, H179, C238, C242, and G245.

\* \* \* \* \*